US012213654B2

(12) United States Patent     (10) Patent No.: US 12,213,654 B2
Freedman et al.     (45) Date of Patent: Feb. 4, 2025

(54) PHASE IDENTIFICATION OF ENDOSCOPY PROCEDURES

(71) Applicant: Verily Life Sciences LLC, South San Francisco, CA (US)

(72) Inventors: Daniel Freedman, Haifa (IL); Ehud Rivlin, Haifa (IL); Valentin Dashinsky, Tirat Carmel (IL); Roman Goldenberg, Haifa (IL); Liran Katzir, Haifa (IL); Dmitri Veikherman, Ness Ziona (IL)

(73) Assignee: Verily Life Sciences LLC, Dallas, TX (US)

( * ) Notice: Subject to any disclaimer, the term of this patent is extended or adjusted under 35 U.S.C. 154(b) by 502 days.

(21) Appl. No.: 17/564,007

(22) Filed: Dec. 28, 2021

(65) Prior Publication Data

US 2022/0369920 A1     Nov. 24, 2022

Related U.S. Application Data

(60) Provisional application No. 63/192,420, filed on May 24, 2021.

(51) Int. Cl.
*A61B 1/31* (2006.01)
*A61B 1/00* (2006.01)
(Continued)

(52) U.S. Cl.
CPC .......... *A61B 1/31* (2013.01); *A61B 1/000096* (2022.02); *A61B 1/00043* (2013.01);
(Continued)

(58) Field of Classification Search
CPC ... A61B 1/31; A61B 1/000096; A61B 1/0043; A61B 1/00087; A61B 1/05;
(Continued)

(56) References Cited

U.S. PATENT DOCUMENTS

2006/0293558 A1* 12/2006 De Groen ............. G06T 7/0012
                                                                      600/101
2018/0225820 A1* 8/2018 Liang ...................... G16H 30/40
(Continued)

FOREIGN PATENT DOCUMENTS

| WO | 2020242949 A1 | 12/2020 |
|---|---|---|
| WO | 2020245815 A1 | 12/2020 |
| WO | 2021011190 A1 | 1/2021 |

OTHER PUBLICATIONS

International Search Report and Written Opinion, mailed Aug. 17, 2022, in corresponding International Patent Application No. PCT/US2022/30524, 9 pages.

(Continued)

*Primary Examiner* — Juan A Torres
(74) *Attorney, Agent, or Firm* — Christensen O'Connor Johnson Kindness PLLC

(57) ABSTRACT

Embodiments of a system, a machine-accessible storage medium, and a computer-implemented method are described in which operations are performed. The operations comprising receiving a plurality of image frames associated with a video of an endoscopy procedure, generating a probability estimate for one or more image frames included in the plurality of image frames, and identifying a transition in the video when the endoscopy procedure transitions from a first phase to a second phase based, at least in part, on the probability estimate for the one or more image frames. The probability estimate includes a first probability that one or more image frames are associated with a first phase of the endoscopy procedure.

21 Claims, 9 Drawing Sheets

(51) Int. Cl.
   *A61B 1/05* (2006.01)
   *G06T 7/00* (2017.01)
   *G06T 7/143* (2017.01)
(52) U.S. Cl.
   CPC ............ *A61B 1/00087* (2013.01); *A61B 1/05* (2013.01); *G06T 7/0012* (2013.01); *G06T 7/143* (2017.01); *G06T 2207/10068* (2013.01); *G06T 2207/20084* (2013.01); *G06T 2207/30028* (2013.01); *G06T 2207/30032* (2013.01)
(58) Field of Classification Search
   CPC .......... A61B 1/00006; A61B 1/000094; A61B 1/0005; A61B 1/00055; G06T 7/0012; G06T 7/143; G06T 2207/10068; G06T 2207/20084; G06T 2207/30028; G06T 2207/30032
   USPC ........................................................ 382/128
   See application file for complete search history.

(56) References Cited

U.S. PATENT DOCUMENTS

| | | | |
|---|---|---|---|
| 2018/0253839 A1* | 9/2018 | Zur ................... | A61B 1/000094 |
| 2019/0297276 A1* | 9/2019 | Sachdev ................ | G16H 30/40 |
| 2019/0362834 A1 | 11/2019 | Venkataraman et al. | |
| 2021/0038066 A1* | 2/2021 | Bos .................... | A61B 1/00045 |
| 2021/0133964 A1 | 5/2021 | Sachdev et al. | |
| 2021/0378484 A1* | 12/2021 | Ninh .................. | A61B 1/00009 |
| 2022/0202502 A1* | 6/2022 | Zhang .................... | A61B 34/20 |

OTHER PUBLICATIONS

Freedman et al., "Detecting Deficient Coverage in Colonoscopies", IEEE Transactions on Medical Imaging, 2020.
Freedman et al., "Detecting Deficient Coverage in Colonoscopies", arXiV 2001. 08589 v3, Mar. 29, 2020.
Ma et al., "Real-Time 3D Reconstruction of Colonscopic Surfaces for Determining Missing Regions", Springer Nature Switzerland AG, 2019.
Aghanouri et al., "New image-guided method for localisation of an active capsule endoscope in the stomach", The Institution of Engineering and Technology, Sep. 19, 2019.
Almalioglu et al., "GANVO: Unsupervised Deep Monocular Visual Odometry and Depth Estimation with Generative Adversarial Networks", arXiv:1809.05786v3, Mar. 5, 2019.
Ballesteros et al., "Automatic Classification of Non-informative Frames in Colonoscopy Videos using Texture Analysis", Conference Paper in Lecture Notes in Computer Science, Feb. 2017.
Barclay et al., "Colonoscopic Withdrawal Times and Adenoma Detection during Screening Colonoscopy", The New England Journal of Medicine, 2006.
Cheng et al., "Comparison of polyp detection during both insertion and withdrawal versus only withdrawal of colonoscopy: A prospective randomized trial", Journal of Gastroenterology and Hepatology, 2019.
Cho, "A Novel Summary Report of Colonoscopy: Timeline Visualization Providing Meaningful Colonoscopy Video Information", Seoul National University, Aug. 2019.
Cho et al., "Identification of cecum time-location in a colonoscopy video by deep learning analysis of colonoscope movement", Creative Commons, Open Access, Jul. 29, 2019.
Colorectal cancer, World Health Organization, International Agency for Research on Cancer, Globocan 2020.
Dietterich et al., "Solving the multiple instance problem with axis-parallel rectangles", Artificial Intelligence, 89, 1997.
Farha et al., MS-TCN: Multi-Stage Temporal Convolutional Network for Action Segmentation, arXiv:1903.01945v2 ; [CS.CV] Apr. 2, 2019.
Fraundofer, et al. Visual Odometry: Part II-Matching, Robustness, and Applications, IEEE Robotics & Automation Magazine, May 18, 2014.
Friedman, Greedy Function Approximation: A Gradient Boosting Machine, The Annals of Statistics, 2001, vol. 29 No. 5.
Friedman, Stochastic gradient boosting, Elsevier, Computational Statistics & Data Analysis 38 (2002).
Garg et al., Unsupervised CNN for Single View Depth Estimation: Geometry to the Rescue, arXiv:1603.04992v2 [cs.CV] Jul. 29, 2016.
Gordon et al., Depth from Videos in the Wild: Unsupervised Monocular Depth Learning from Unknown Cameras, Apr. 10, 2019.
He et al., Deep Residual Learning for Image Recognition, arXIV:1512.03385v1, Dec. 10, 2015.
Horn et al. Determining Optical Flow, Artificial Intelligence 1981.
Powering the Future of Digital Surgery, Verily, Johnson & Johnson, May 24, 2021.
Kaminski et al., Increased Rate of Adenoma Detection Associates with Reduced Risk of Colorectal Cancer and Death, http://dx.doi.org/10.1053/j.gastro.2017.04.006, Jul. 2017.
Lee et al., An Adequate level of training for technical competence in screening and diagnostic colonoscopy: a prospective multicenter evaluation of the learning curve, www.giejournal.org, vol. 67, No. 4: 2008, Gastrointestinal endoscopy.
Lee et al., Longer mean colonoscopy withdrawal time is associated with increased adenoma detection: evidence from the Bowel Cancer Screening Programme in England, Endoscopy, 2013.
Li et al., UnDeepVO: Molecular Visual Odometry through Unsupervised Deep Learning, arXiv:1709.06841v2, Feb. 21, 2018.
Mahjourian et al., Unsupervised Learning of Depth and Ego-Motion from Monocular Video using 3D Geometric Constraints, arXiv:1802.05522v2, Jun. 9, 2018.
Pinheiro et al., Deep Homography Based Localization on Videos of Endoscopic Capsules, https://www.researchgate.net/publication/330937767, 2018 IEEE International Conference on Bioinformatics and Biomedicine, Dec. 2018.
Scaramuzza et al., Visual Odometry, IEEE Robotics & Automation Magazine, Dec. 2011.
Simmons et al., Impact of endoscopist withdrawal speed on polyp yield: implications for optimal colonoscopy withdrawal time, Alimentary Pharmacology & Therapeutics, Jul. 5, 2006.
Twinanda et al., EndoNet: A Deep Architecture for Recognition Tasks on Laparoscopic Videos, arXiv:1602.03012v2, May 26, 2016.
Ummenhofer et al., DeMoN: Depth and Motion Network for Learning Monocular Stereo, arXiv:1612.02401v2, Apr. 11, 2017.
Urban et al., Deep Learning Localizes and Identifies Polyps in Real Time with 96% Accuracy in Screening Colonoscopy, Gastroenterology Oct. 1, 2019.
Wang et al., A Novel Relative Position Estimation Method for Capsule Robot Moving in Gastrointestinal Tract, www.mdpi.com/journal/sensors, Jun. 19, 2019.
Wang et al., DeepVO: Towards End-to-End Visual Odometry with Deep Recurrent Convolutional Neural Networks, Sep. 25, 2017.
Wang et al., Development and validation of a deep-learning algorithm for the detection of polyps during colonscopy, nature biomedical engineering, https://doi.org/10.1038/s41551-018-0301-3, vol. 2, Oct. 2018.
Yang et al., Deep Virtual Stereo Odometry: Leveraging Deep Depth Prediction for Monocular Direct Sparse Odometry; arXiv:1807.02570v2, Jul. 25, 2018.
Yin et al., GeoNet: Unsupervised Learning of Dense Depth, Optical Flow and Camera Pose, arXiv:1803.02276v2, Mar. 12, 2018.
Yun et al., Colonoscopic withdrawal time and adenoma detection in the right colon, Observational Study, Medicine Open, Aug. 6, 2018.
Zhan et al., Unsupervised Learning of Monocular Depth Estimation and Visual Odometry with Deep Feature Reconstruction, arXiv:1803.03893v3, Apr. 5, 2018.
Zhou et al., DeepTAM: Deep Tracking and Mapping, arXiv:1808.01900v2, Aug. 7, 2018.
Zhou et al., Unsupervised Learning of Depth and Ego-Motion from Video, arXiv:1704.07813v2, Aug. 1, 2017.

(56) References Cited

OTHER PUBLICATIONS

Cancer Facts & Figures 2019, American Cancer Society, https://www.cancer.org/research/cancer-facts-statistics/al-cancer-facts-figures/cancer-facts-figures-2019.html; downloaded from web on Sep. 16, 2021.
Freedman et al., Detecting Deficient Coverage in Colonoscopies, IEEE Transactions on Medical Imaging, vol. 39, No. 11, Nov. 2020.
Freedman et al., Using Machine Learning to Detect Deficient Coverage in Colonscopy Screenings, https:///ai.googleblog.com/2020/08/using-machine-learning-to-detect.html; Aug. 28, 2020.
SCOPEPILOT—The Next Generation 3D colon navigation system, Pentax Medical, May 24, 2021, date downloaded from web https://www.pentaxmedical.com/pentax/en/95/2/SCOPEPILOT-The-next-generation-3D-colon-navigation-system.

\* cited by examiner

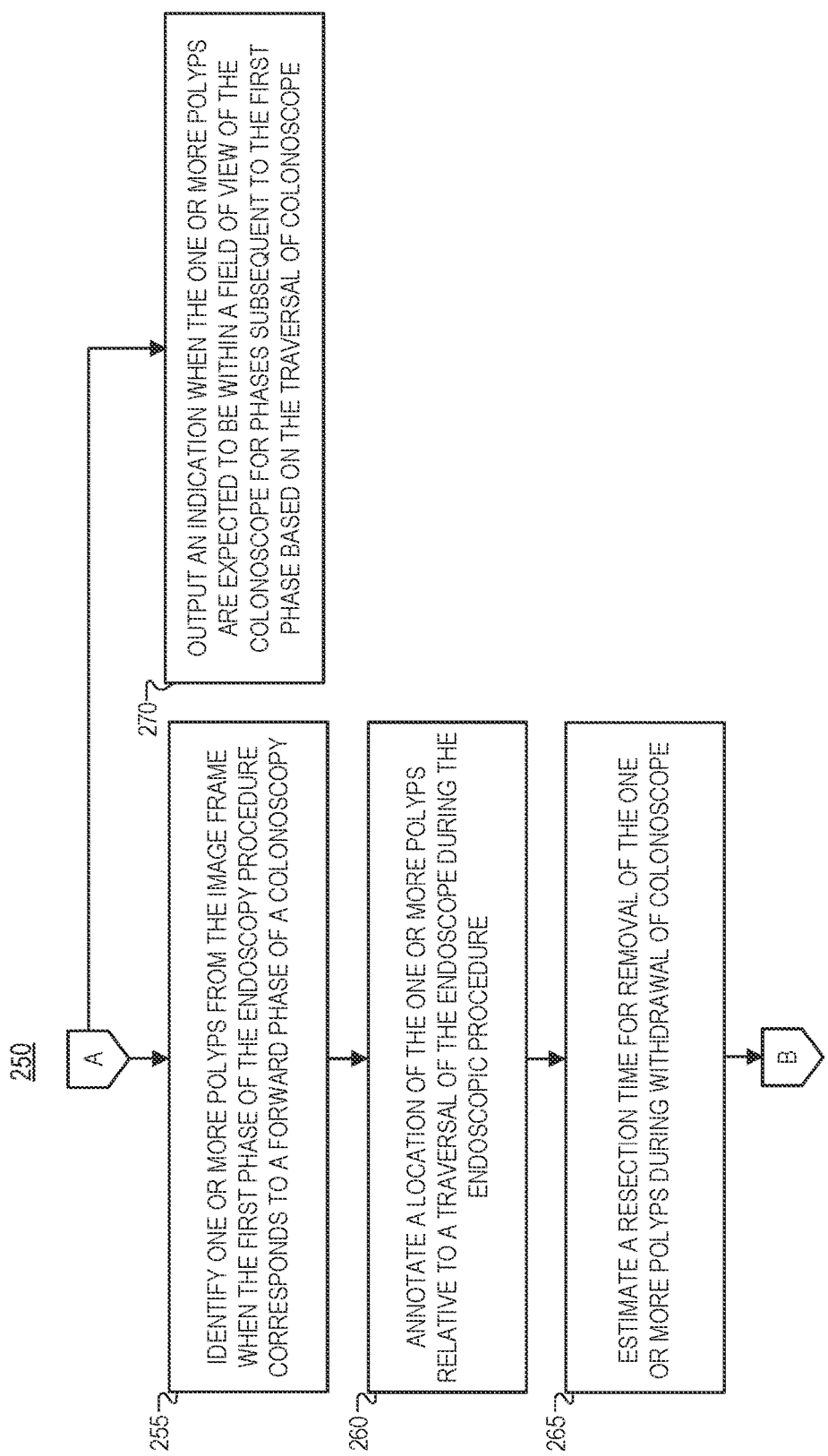

PHASE IDENTIFICATION OF ENDOSCOPY PROCEDURES

CROSS-REFERENCE TO RELATED APPLICATIONS

This application claims the benefit of U.S. Provisional Application No. 63/192,420, filed on May 24, 2021, the contents of which are incorporated herein by reference.

TECHNICAL FIELD

This disclosure relates generally to endoscopy procedures, and in particular, but not exclusively, to colonoscopy phase identification from video or image data.

BACKGROUND INFORMATION

Endoscopy procedures involve insertion of an endoscope into a body to examine the interior of a hollow organ or a cavity of the body such as the gastrointestinal tract, the respiratory tract, the ear, the urinary tract, the female reproductive system, or cavities that are normally closed but have been opened via an incision. A cutting tool or other attachment may be coupled to the endoscope to perform medical procedures such as tissue biopsies, variceal banding, polyp removal, or otherwise. For example, during a colonoscopy, the colon is visually examined with a colonoscope to determine whether polyps are present and, if necessary, remove the polyps, which may help prevent colorectal cancer.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 2A and 2B illustrates an example method for phase identification of an endoscopy procedure, in accordance with an embodiment of the present disclosure.

DETAILED DESCRIPTION

Figure 1A:
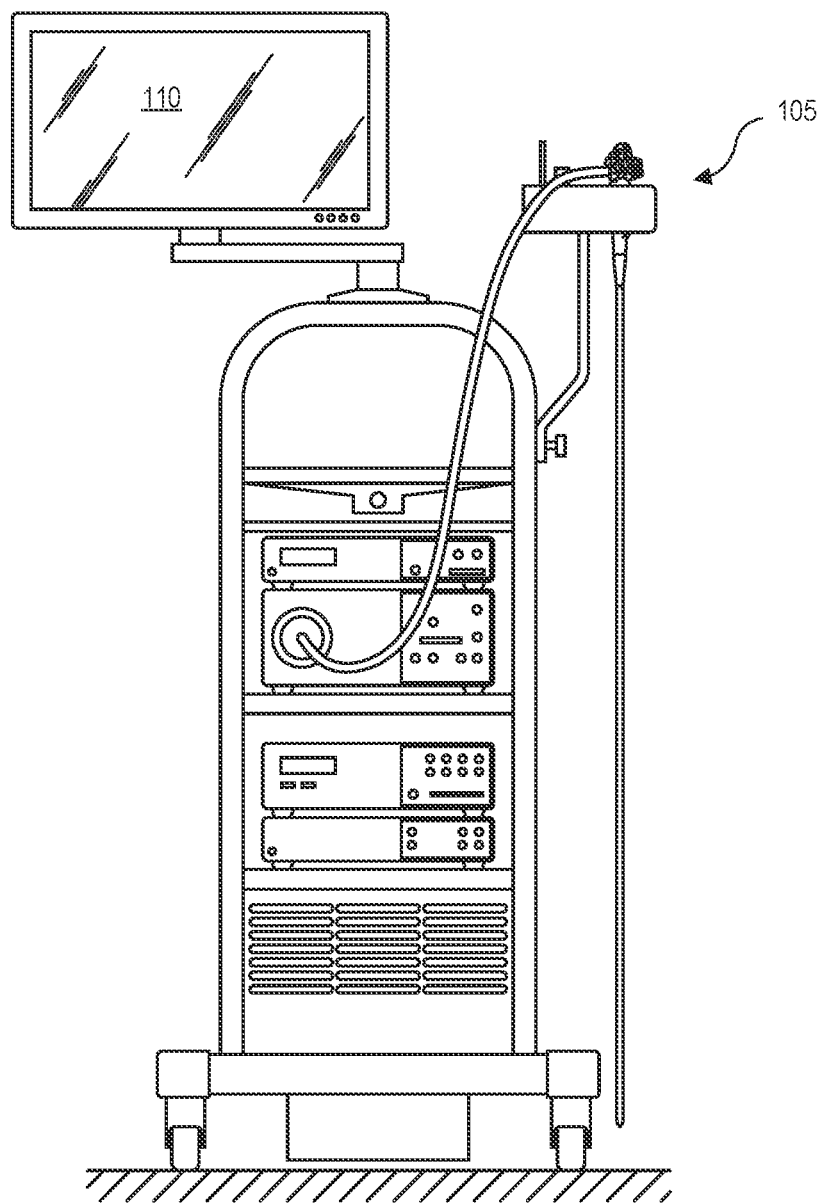
FIG. 1A illustrates a colonoscopy tower system, in accordance with an embodiment of the disclosure.

Embodiments of a system, apparatus, and method for phase identification of endoscopy procedures are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein are embodiments of an apparatus, a system, and a method for phase identification of endoscopic procedures based on image or video data. Specifically, the phase identification will be discussed in the context of a colonoscopy. However, it is appreciated that phase identification is not limited to colonoscopies and that phase identification of other types of endoscopy procedures may also be determined with the embodiments described herein. Accordingly, it is appreciated specific instances of the terms "colonoscopy", "colonoscope", or "colon" may be swapped throughout the detailed description for their more generic counterparts of "endoscopy," "endoscope," or "cavity or tubular anatomical structure," respectively. It is further appreciated that endoscopy procedures are not limited to examination and/or exploration of the colon, but rather is generally applicable to endoscopy procedures in which the gastrointestinal tract, the respiratory tract, the ear, the urinary tract, the female reproductive system, cavities that are normally closed but have been opened via an incision, or other hollow organs or cavities of a body are explored, examined, and/or have one or more surgical procedures performed therein or thereon with the aid of a medical instrument including a camera that can be introduced into the body.

Endoscopy procedures typically include multiple phases or stages defined by actions (or inaction) performed with an endoscope. The phases may be characterized by movement of the endoscope (or lack thereof), elapsed duration of a given phase, medical procedure performed with the endoscope (e.g., cutting, resection, cauterization, or the like), or any other distinctive operation performed during the endoscopy procedure. For example, a colonoscopy may include a forward phase, a stagnant phase, a backward phase, and a resection phase. During the forward phase a colonoscope is predominantly moved forward (i.e., +z direction) through the rectum until reaching the end of the colon, known as the cecum. The time it takes to reach the cecum is known as the Cecal Intubation Time (CIT). The forward phase may be very challenging since several flexures must be traversed for the colonoscope to reach the cecum, which may require intermittent forward and backward motion of the colonoscope. Once the cecum has been reached, the stagnant phase of the colonoscopy occurs in which a visual examination of the cecum is performed and there is little to no motion of the colonoscope (e.g., the z-position of the colonoscope may be confined to a certain range as the colonoscope looks around the cecum). Once the cecum has been examined, the backward phase of the colonoscopy occurs in which the colonoscope is slowly extracted (i.e., -z direction) from the body. During the backward phase, the goal is typically to detect, examine, and remove polyps.

The collective duration of the stagnant and the backward phases of the colonoscopy corresponds to the Colonoscopic Withdrawal Time (CWT), which can impinge directly upon successful detection and removal of polys. To be more specific, the success in polyp detection is often measured by the Adenoma Detection Rate (ADR), which is defined as the fraction of procedures in which a physician discovers at least one adenomatous polyp. As there is expected to be positive correlation between CWT and the rates of neoplasia detection, current guidelines recommend that the CWT be at least 6 minutes in order to achieve the desired higher ADR. Higher ADR is directly linked to lower rates of interval colorectal cancer (CRC), thus ensuring a sufficiently high CWT is of paramount importance. However, without phase identification of the various phases of the colonoscopy it may be difficult to determine the CWT in an objective manner. Moreover, videos of the colonoscopy may not include annotations indicating which portions of the video correspond to which phases of the colonoscopy making it difficult to extract the CWT directly from the video.

Described herein are embodiments that may be implemented in an apparatus, system, or method to estimate the phases of a colonoscopy (or more generally endoscopy procedures) from a video of the colonoscopy. More succinctly, image frames of the video may be mapped, annotated, examined, or otherwise processed to determine when (e.g., at which image frame and/or elapsed time of the video) the colonoscopy transitions from the forward phase to the stagnant and/or backward phases such that CWT may be calculated. In some embodiments, features may be extracted from the image frames (e.g., to reduce the dimensionality of the image frames of the video) such as egomotion data of the camera capturing the video (e.g., relative motion such as translation and rotation), depth information (e.g., a depth map is generated from a given image frame), and landmark presence data (e.g., whether one or more anatomical landmarks are observed within a given image frame of the video). In some embodiments the features extracted may then be utilized to perform temporal segmentation of the video to determine which portions of the video correspond to which phases of the colonoscopy. Subsequently, once the video has been segmented, other features characterizing the colonoscopy (e.g., CWT, a performance metric of the colonoscopy, or the like) may be calculated or otherwise determined. Additionally, in some embodiments, the temporal segmentation of the video may be utilized to assist in situ during the colonoscopy. For example, a polyp detection system may be utilized to identify polyps during the forward phase with the approximate location within the colon of the identified polyps marked based on the egomotion data (e.g., z-position), then during the backward phase an indication may be provided to the physician performing the colonoscopy when the identified polyps are expected to be observed (e.g., when the egomotion data indicates that the colonoscope has returned to the z-position where the polyp was originally identified during the forward phase).

FIG. 1A illustrates a colonoscopy tower system 100, in accordance with an embodiment of the disclosure. System 100 illustrates an example hardware system in which phase estimation of the colonoscopy may be provided (e.g., in situ). System 100 includes an endoscope or colonoscope 105 coupled to a display 110 for capturing images of a colon and displaying a live video feed of the colonoscopy procedure. In one embodiment, the image or video analysis and user interface overlays described herein may be performed and generated by a processing box that plugs in between the colonoscope 105 and display 110.

Figure 1B:
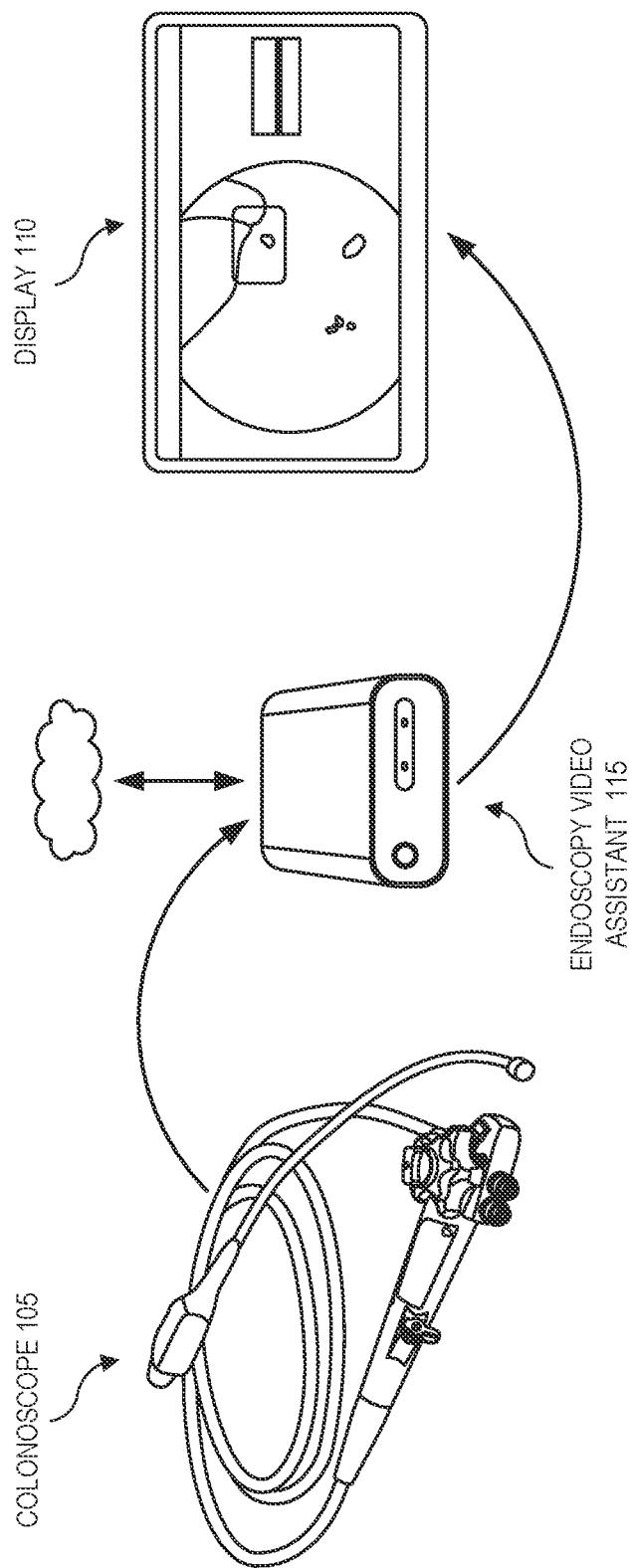
FIG. 1B illustrates an endoscopy video assistant capable of generating a colonoscopy user-interface for real-time phase identification and visual cues, in accordance with an embodiment of the disclosure.

FIG. 1B illustrates an example endoscopy video assistant (EVA) 115 capable of phase estimation, temporal segmentation, and generating a colonoscopy user interface (UI) overlay described herein. EVA 115 may include the necessary processing hardware and software, including machine learning models, to perform the real-time image processing and UI overlays. For example, EVA 115 may include a data storage, a general-purpose processor, graphics processor, and video input/output (I/O) interfaces to receive a live video feed from colonoscope 105 and output the live video feed within a UI that overlays various visual aids and data associated with the colonoscopy or other endoscopy procedures. In some embodiments, EVA 115 may further include a network connection for offloading some of the image processing and/or reporting and saving data for individual patient recall and/or longitudinal, anonymized studies. The colonoscopy UI may include the live video feed reformatted, parsed, or scaled into a video region (e.g., video region 155 in FIG. 1C), or may be a UI overlay on top of an existing colonoscopy monitor feed to maintain the original format, resolution, and integrity of the colonoscopy live video feed.

Figure 1C:
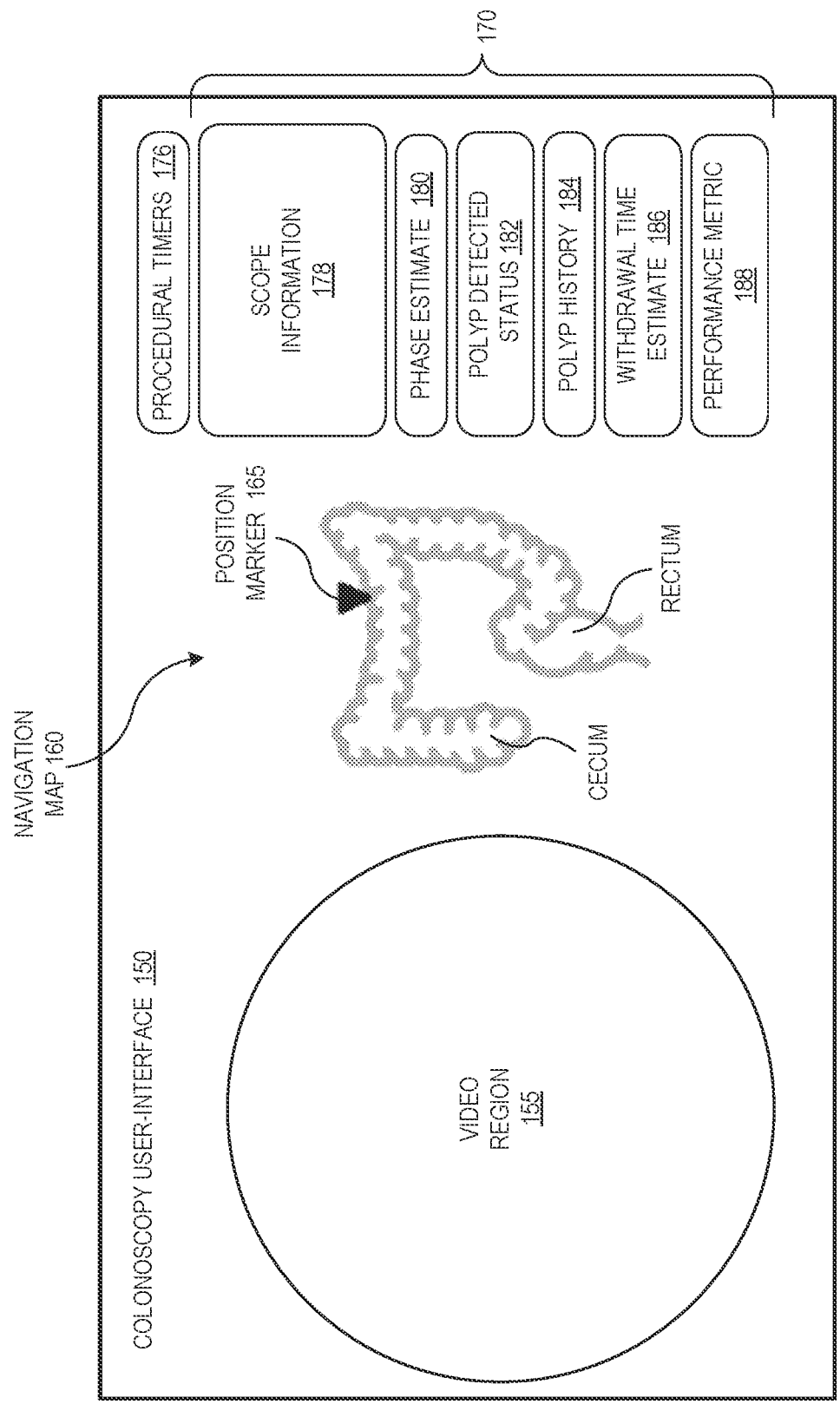
FIG. 1C illustrates a colonoscopy user-interface for visualizing a colonoscopy procedure during or after the colonoscopy is performed, in accordance with an embodiment of the disclosure.

FIG. 1C illustrates a colonoscopy UI 150 for visualizing a colonoscopy procedure, in accordance with an embodiment of the disclosure. The colonoscopy UI 150 is one possible implementation output by EVA 115 to be rendered on display 110 illustrated in FIG. 1A or FIG. 1B. Referring back to FIG. 1C, the illustrated embodiment of colonoscopy UI 150 includes a video region 155 for displaying a colonoscopy video (e.g., live or otherwise), a navigation map 160 with a position marker 165, and a region for procedure data 170. The illustrated embodiment of procedure data 170 includes procedural timers 176, scope information 178, a phase estimate 180, a polyp detected status 182, a polyp detected history 184, a withdrawal time estimate 186, and a performance metric 188. It is appreciated that the illustrated embodiment of colonoscopy UI 150 should not be deemed limiting, but rather in other embodiments the illustrated elements of the user-interface may be rearranged or omitted. Additionally, in other embodiments of the colonoscopy UI 150, additional elements may be included in the user-interface (e.g., a coverage map of the colonoscopy). It is further noted that the elements shown in colonoscopy UI 150 may be tailored to the specific function being performed. For example, the user-interface for bulk analysis and review of colonoscopy videos may be different than the user interface used during a live colonoscopy.

In the illustrated embodiment of FIG. 1C, the video region 155 provides a region within colonoscopy UI 150 to display a video (e.g., a live video feed from an endoscope, a video pulled from an endoscopy database, or otherwise). For example, the video region 155 may display the interior of a colon captured during a colonoscopy procedure by an image sensor of colonoscope 105. In other words, video region 155 may be used to display the real-time field of view (FOV) captured by the image sensor of colonoscope 105. Although video region 155 is illustrated as having a round FOV, in other embodiments, the FOV may be rectangular, square, or otherwise.

Navigation map 160 depicts longitudinal sections of the colon. Each longitudinal section represents a different depth into the colon (or large intestine) extending from the rectum or anal canal to the cecum. The endoscope (e.g., colonoscope) traverses through the longitudinal sections of the colon (i.e.,+z-direction) from the rectum towards the cecum during the colonoscopy. Navigation map 160 may be implemented as an anatomical atlas or caricature being representative of the colon, or an actual three-dimensional (3D) model of the colon to visually indicate various information obtained through analysis of the video (e.g., images output by the colonoscopy that may or may not be displayed on the video region 155). In one embodiment, egomotion data extracted from the video may be utilized to predict a relative or absolute position of the distal end of the colonoscope for one or more image frames of the video. The expected position of the colonoscope may then be visually indicated (e.g., in real-time or otherwise) on the navigation map 160 via position marker 165 when the one or more image frames are being displayed in the video region 155. In the same or other embodiments, other information may be visually indicated with the navigation map 160. In one embodiment, the image frames of the video may be analyzed to determine whether a polyp is observed during the insertion or forward phase of the colonoscopy. When one or more polyps are observed, the z-position of a given one of the polyps may be visually indicated on the navigation map 160 such that during the withdrawal phase (e.g., backward phase) of the colonoscopy the physician, endoscopist, or other individual is provided an indication when the one or more polyps are expected to be in a field of view of the colonoscope.

As illustrated in FIG. 1C, colonoscopy UI 150 includes a region for displaying procedure data 170. The illustrated embodiment of procedure data 170 includes procedural timers 176, scope information 178, phase estimate 180, polyp detected status 182, polyp detected history 184, withdrawal time estimate 186, and performance metric 188.

Procedural timer(s) 176 may include one or more timers that track the overall procedure time since commencement of the colonoscopy (e.g., forward phase, stagnant phase, insertion phase), track the procedure time of just the forward phase (e.g., insertion of the colonscope into the rectum until reaching the cecum), or track the procedure time since commencement of the withdrawal phase (e.g., once the cecum has been reached by the colonoscope). Scope information 178 may include metadata pertinent to the particular colonoscope 105 such as camera resolution, software/firmware version, frame rate, color space, etc.

Phase estimate 180 may display an expected phase (e.g., forward, stagnant, backward) of the colonoscopy for the image being shown in the video region 155. In other words, during a live colonoscopy, the phase estimate 180 may provide an expected phase of the colonoscopy in real-time based on analysis of the video of the colonoscopy using one or more machine learning models, deep neural networks, or otherwise.

Polyp detected status 182 represents an indication of whether the image analysis and polyp detect software has detected a polyp in the current FOV or live image feed currently displayed in video region 155. In the same or other embodiments, the polyp detected status 182 may also indicate whether a polyp is expected to in field of view of the colonoscopy during the withdrawal of the colonoscope (e.g., based on the z-position of the colonoscope and a polyp being observed during the forward phase) even if the current field of view of the colonoscope displayed on the video region 155 does not show a polyp. This indication may serve as an alert to the endoscopist that a polyp is expected to be observed at the current z-position of the colonoscope and if a polyp is not in the field of view of the colonoscope then the colonoscope may need to be reoriented or otherwise repositioned in order to view the polyp.

Polyp detected history 184 represents a count of the overall number of detected polyps. Additionally, polyp detected history 184 may include a selectable menu for displaying further information regarding the particular detected polyps. For example, if a classifier is applied to perform optical biopsies on the detected polyps, then the results of the optical biopsy may be accessed via the polyp detected history 184 by selecting a given polyp. Alternatively, optical biopsy results and/or reference images for comparison may automatically appear when a polyp is identified in the FOV. The results may include a classification of benign, precancerous, cancerous, etc. along with display of a confidence interval. In yet other embodiments, the classification may include other classifications such as hyperplastic polyp, adenomatous polyp, etc.

Withdrawal time estimate 186 displays an estimated withdrawal time (e.g., the collective time of the stagnant and backward phases corresponding to CWT) to complete the withdrawal phase of the colonoscopy procedure. The withdrawal time may be estimated with a machine learning model including one or more deep neural networks to analyze the video of the colonoscopy (e.g., the collective images output by the video feed displayed on the video region 155). As such, the withdrawal time estimate 186 may not be displayed until after completion of the colonoscopy (i.e., once the video feed ends or otherwise indicates that the colonoscope has exited the rectum). In some embodiments, the withdrawal time estimate 186 may correspond to a net withdrawal time in which time spent removing polyps (i.e., resection) is excluded from the withdrawal time estimate.

Performance metric 188 provides a metric characterizing a performance of the colonoscopy based on the withdrawal time estimate 186. In some embodiments, the performance metric may indicate a "sufficient" status when the withdrawal time estimate 186 is at least 6 minutes in duration and an "insufficient" status when the withdrawal time estimate 186 is less than 6 minutes in duration. In some embodiments, a duration other than 6 minutes may be utilized when determining whether the colonoscopy was sufficient. In other embodiments the performance metric may also take into account other aspects of the colonoscopy. For example, if one or more polyps were observed by a poly detect system during the forward phase of the colonoscopy but not during the withdrawal phase then the performance metric may be reduced. In one embodiment the performance metric may be a singular binary value (e.g., 0 or 1), a scalar (e.g., a number from 0 to 1), or any other characteristic quantity that may indicate performance. In the same or other embodiments, the performance metric may have multiple values (e.g., a first value associated with the withdrawal time estimate, a second value associated with whether the same number of polys were observed during the forward phase and the backwards or withdrawal phases, and so on).

Figure 2A:
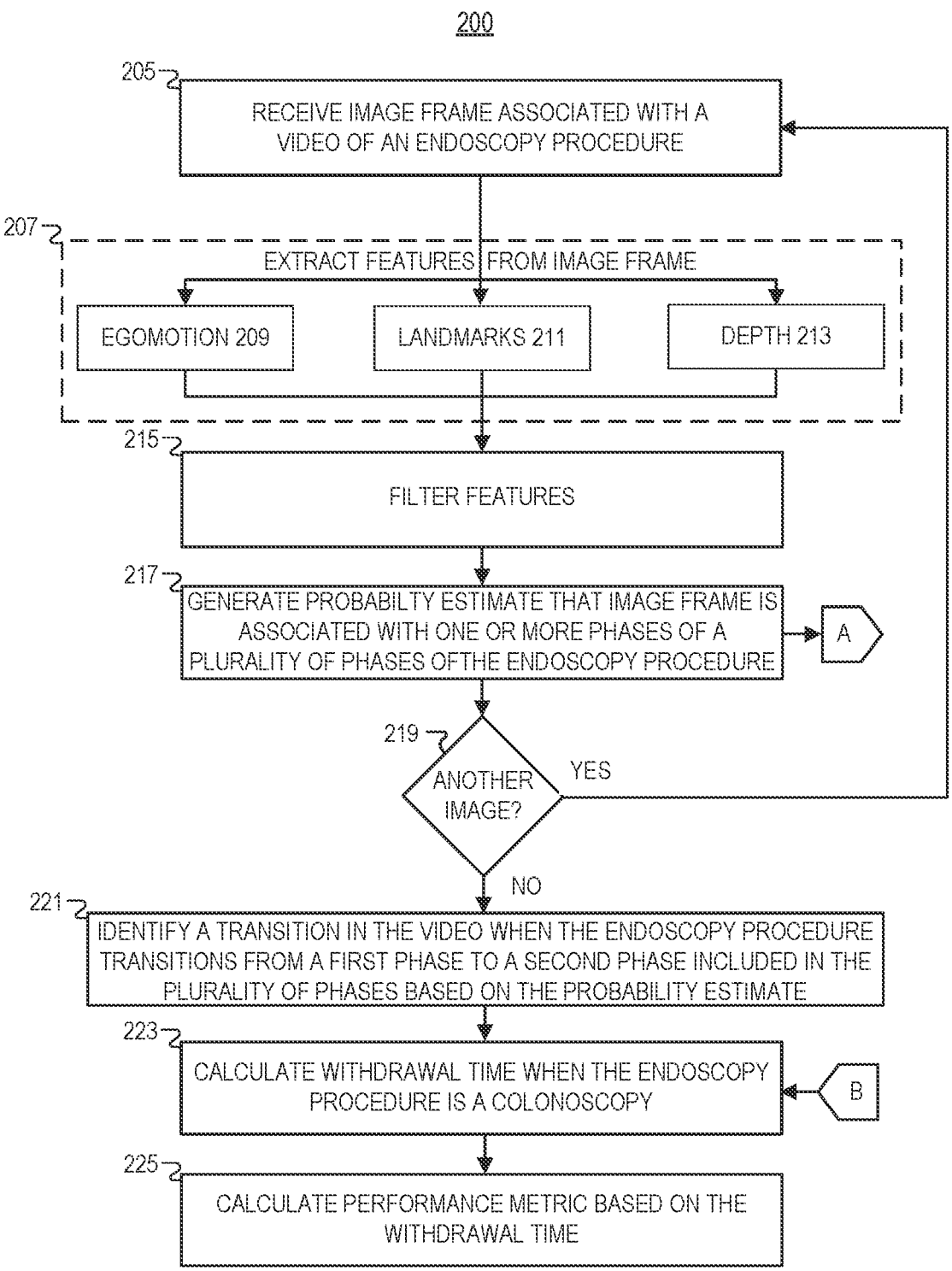

FIGS. 2A and 2B illustrate an example method 200 for phase identification of an endoscopy procedure, in accordance with an embodiment of the present disclosure. Method 200 may be implemented by the colonoscopy tower system 100 illustrated in FIG. 1A, the endoscopy video assistant 115 illustrated in FIG. 1B, or more generally a computing device such as computing device 600 illustrated in FIG. 6, in accordance with embodiments of the disclosure. In the same or other embodiments, the method 200 may be a computer-implemented method including instructions provided by at least one machine-accessible storage medium (e.g., non-transitory memory) that when executed by a machine (e.g., a computer, a computing device, or otherwise), will cause the machine to perform operations for phase identification of an endoscopy procedure (e.g., a colonoscopy). As illustrated in FIGS. 2A and 2B, method 200 includes blocks 205-270. However, it is appreciated that the order in which some or all of the process blocks appear in the method 200 should not be deemed limiting. Rather, one of ordinary skill in the art having the benefit of the present disclosure will understand that some of the process blocks may be executed in a variety of orders not illustrated, or even in parallel.

Referring to FIG. 2A, block 205 shows receiving a plurality of image frames associated with a video of an endoscopy procedure (e.g., a colonoscopy procedure). The video may correspond to a video feed from an endoscope (e.g., a live video feed received during an endoscopy procedure) or a video obtained through other means (e.g., through a video database that includes endoscopy videos or any other computer or machine-readable medium containing endoscopy videos). It is appreciated that in some embodiments the resolution of the image frame may be equivalent to the original video (e.g., the image frame is a full-resolution image frame). In the same or other embodiments, the image frame may correspond to a downsampled image frame (e.g., reduced resolution relative to the originally captured video) or upsampled image frame (e.g., increased resolution relative to the originally captured video). The image frame may have a color (e.g., RGB, CMYK, or otherwise), grayscale, or black and white color space. It is appreciated that in some embodiments the color space of the image frame may match the color space from the video from which the image frame is obtained or be processed (e.g., extract grayscale images from a color video).

As discussed above, the endoscopy procedure may include a plurality of phases including a first phase, a second phase, a third phase, more phases, or less phases. In an embodiment where the endoscopy procedure corresponds to a colonoscopy, the first phase may correspond to a forward phase in which the endoscope or colonoscope is inserted into the rectum and pushed along a z-direction (i.e., longitudinal axis of the colon) until reaching the cecum. More specifically, the forward phase is characterized predominantly by forward motion (e.g., +z-direction) of the colonoscope from a rectum toward a cecum. The second phase may correspond to a stagnant phase in which the endoscope or colonoscope remains relatively motionless (e.g., with regard to the z-position) while the endoscopist examines the area or cavity corresponding to the cecum. The third phase may correspond to the backward phase in which the endoscope or colonoscope is withdrawn from the cecum toward the rectum. More specifically, the backward phase is characterized predominately backward motion (e.g., −z-direction) of the colonoscope from the cecum to toward the rectum.

Block 207 illustrates extracting different features from the image frame. The different features may be extracted to reduce the dimensionality of the image frame while simultaneously characterizing the image frame in a manner that can be compared with other image frames in the video or used to determine one or more attributes (e.g., phase of endoscopy procedure when the image frame was captured) with a reduced computational burden. In the illustrated embodiment, the different features that may be extracted include at least one of egomotion data 209, landmark presence data 211, or depth information 213. In other embodiments the different features include at least two features selected from a group including egomotion data 209, landmark presence data 211, and depth information 213. It is appreciated that by extracting features from the image frame, a reduced dimensional representation (e.g., corresponding to the features) of the image frame may be utilized to characterize the image frame as belonging to one or more phases of the plurality of phases of the endoscopy procedure. For example, a color image frame having a resolution of 256×256 RGB pixels includes almost 200,000 values (256*256*3), which can be reduced by the different features. In other words, the different features characterize the image frame with a reduced representation relative to a pixel value quantity of the image frame.

In some embodiments, the different features will be extracted with a machine learning model or algorithm including a plurality of deep neural networks. In one embodiment, the machine learning model will output the different features characterizing the image frame in response to the machine learning model receiving the image frame. In some embodiments, the different features are determined on a per-frame basis (e.g., as illustrated by the loop corresponding to blocks 205-219) with each feature included in the different features associated with a corresponding neural network included in the plurality of deep neural networks.

Block 209 represents extracting egomotion data 209 from the image frame. The egomotion data 209 corresponds to an estimated motion of an endoscope camera associated with capture of the image frame. For example, as the colonoscope moves through the colon, motion of the colonoscope (or more specifically, the image sensor of the colonoscope capturing the images) can be determined. In some embodiments, the estimated motion is relative and taken in reference to a preceding image frame (e.g., an image frame captured previously relative to the image frame). In one embodiment, the estimated motion is based on consecutive pairs of image frames (e.g., the image frame and an immediately prior image frame). It is appreciated that the egomotion data allows for assessment in which direction the colonoscope is moving to provide a differentiator between the colonoscopic insertion phase and the colonoscopic withdrawal phase.

In some embodiments, a first deep neural network included in the plurality of deep neural networks is used to extract egomotion data included in the different features. In one embodiment, the first deep neural network is or otherwise includes a convolutional neural network (CNN) trained to receive the image frame and the immediately prior image frame associated with the video and in response output the egomotion data. In the same or other embodiments, the egomotion data includes 3 translation coordinates (x, y, z) and 3 rotation coordinates ($\phi_x$, $\phi_y$, $\phi_z$), which are Euler angles. Accordingly, the egomotion data for the image frame reflects the camera motion with respect to the camera coordinates.

Block 211 illustrates extracting landmark presence data from the image frame. More specifically, the landmark presence data indicates whether a view of one or more anatomical landmarks associated with the endoscopy procedure are identified as being included in the image frame. In other words, the landmark presence data indicates whether one or more anatomical landmarks are observed in the image frame. In the case of a colonoscopy, the one or more anatomical landmarks include at least one of an appendiceal orifice, a triradiate fold, or an ileocecal valve when the endoscopy procedure corresponds to a colonoscopy. Advantageously, identifying the presence of the relevant landmarks near the cecum, such as the appendiceal orifice, ileocecal valve, and triradiate fold, provides a strong indication that the colonoscopic withdrawal phase has begun since the appendiceal orifice and triradiate fold are both located within the cecum while the ileocecal valve is located just outside of the cecum.

In some embodiments, a second deep neural network included in the plurality of deep neural networks is utilized to extract the landmark presence data included in the different features. As discussed above, the landmark presence data corresponds to an indication of whether the image frame includes a view of one or anatomical landmarks associated with the endoscopy procedure. In some embodiments, the second deep neural network is includes a dual-head binary classification model to predict the presence of the appendiceal orifice and the triradiate fold within the image frame and a multiple instance learning (MIL) scheme to predict if the image frame includes any distinctive features that are common to the cecum and/or the ileocecal valve. In the same or other embodiments, the dual head classification network for the appendiceal orifice and the triradiate fold and the MIL classifier for the ileocecal valve share a common feature extractor backbone corresponding to a convolutional neural network. It is appreciated that in some embodiments, all networks (e.g., the dual head classification network and the MTh classifier) of the second deep neural network are trained together in an end-to-end fashion.

Block 213 shows extracting depth information from the image frame. In some embodiments, the depth information corresponds to a depth map that replaces pixel data of the image (e.g., red, green, and blue color intensity data) with a corresponding depth estimate. The depth information helps to distinguish between frames in which the camera of the colonoscope is adjacent to the colon (which occur more often in colonoscopic insertion) and frames which see an unobstructed view of the colon (which occur more often in colonoscopic withdrawal). In some embodiments, a third deep neural network included in the plurality of deep neural networks is utilized to extract depth information associated with the image frame. In one embodiment, the third deep neural network is or otherwise includes a convolution neural network.

As illustrated in FIG. 2A, the image frame is provided in parallel to the first deep neural network, the second deep neural network, and the third deep neural network to concurrently determine each of the different features (e.g., egomotion data 209, landmark presence data 211, and depth information 213) for the image frame. However, it is appreciated that in other embodiments, the image frame may not be passed simultaneously to each of the plurality of deep neural networks such that the different features are not extracted concurrently.

Block 215 illustrates optionally filtering the features to compensate for noise that may occur for phase segmentation of the video when the features are analyzed on a per-frame basis. Instead, historical information of the different features may be maintained and used to reduce noise and/or reduce the likelihood of an abrupt change in values for the different features between consecutive image frames. In one embodiment, filtering the features includes applying one or more smoothing filters to the different features to generate smoothed features that aggregate the different features over multiple frames included in the one or more image frames. In one embodiment, the one or more smoothing filters include an exponential-weighted-moving-average of one or more of the different features.

In the same or other embodiments, the exponential-weighted-moving average is of a discrete signal s, denoted by ewma(s), calculated as follows:

$$ewma(s)[0]=0$$

$$ewma(s)[i]=(1-a)\times ewma(s)[i-1]+a\times s[i].$$

In the above, a determines the effective memory span, which a span of m steps using $a=2/m$. It is appreciated that the m steps indicate the number of frames (or pairs of frames), which using information such as frame rate, sample rate, and the like of the video, can be converted to time. For example, if the memory span is indicative of 4 minutes, then the extracted feature being smoothed is based on the moving average inclusive of the previous 4 minutes from when the image frame was captured.

Using the above definition of ewma(s), the different features may be smoothed to reduce noise and/or abrupt changes in values. In one embodiment, the z-translation of the egomotion data is smoothed, where the moving average is taken with a variety of length spans (e.g., 1, 2, 3, and/or 4 minutes), any one of which, or all of which, may be subsequently utilized in determining whether the image frame is associated with one or more phases of the endoscopy procedure. In the same or other embodiments, quantiles (e.g., 0.1, 0.25, 0.5, 0.75, 0.9, or otherwise) may be extracted from the depth map of the image frame. Then, the quantiles may be smoothed using the exponentially weighted moving average with one or more different length spans. In one embodiment, the different length spans for the quantiles of the depth map being smooth includes at least two different length spans (e.g., 2 and 4 minutes). In the same or other embodiments, the landmark presence data extracted from the image frame is smoothed by taking a running maximum (e.g., cumulative maximum) of exponentially weighted moving average of the landmark's probability estimates. In other words, the running average provides an indication as to whether one or more anatomical landmarks have been seen in the image frame and/or any of the previously captured image frames, rather than just the image frame itself, based on the memory span. In some embodiments, the moving average is taken with a variety of length spans such as 8, 15, and 30 seconds.

Block 217 shows generating a probability estimate that the image frame is associated with one or more phases of a plurality of phases of the endoscopy procedure (e.g., the forward, stagnant, and backward phases when the endoscopy procedure is a colonoscopy). In other words, the probability estimate provides an indication or probability that the endoscopy procedure was at any one of the plurality of phases of the endoscopy procedure when the image frame was captured. In some embodiments, the probability estimate is based on the different features extracted from block 207 and/or the filtered features (e.g., smoothed) from block 215. In the same or other embodiments, the probability estimate includes probability values for each of the plurality of phases (e.g., a first probability for a first phase of the endoscopy procedure, a second probability for a second phase of the endoscopy procedure, a third probability for a third phase of the endoscopy procedure, and so on such that the sum of the estimates adds up to 1). For example, when the endoscopy is a colonoscopy, the first probability may indicate whether the colonoscopy was at the forward phase when the image frame was captured, the second probability may indicate whether the colonoscopy was at the stagnant phase when the image frame was captured, and the third probability may indicate whether the colonoscopy was at the backward phase when the image frame was captured.

In some embodiments the probability estimate is generated with a machine learning model including a plurality of deep neural networks to receive the one or more image frames. In other words, the plurality of deep neural networks is utilized to extract the features, which are in turn utilized to generate the probability estimate. In one embodiment, the machine learning model further includes a phase classifier to receive the different features and in response output the probability estimate for the image frame (e.g., on a per-frame basis as illustrated by the loop formed by blocks 205-219). In the same or other embodiments, the machine learning model may include a classifier to receive the features (as extracted in block 207, filtered in block 215, or a combination thereof) and generate as an output the probability estimate. In one embodiment, gradient boosted decision trees are used in combination with the filtered features to generate the probability estimate for the image frame. However, in other embodiments, a deep-learning model may also be used to generate the probability estimate. In an embodiment where gradient boosted decision trees are utilized to generate the probability estimate, the resulting model is trained with training data of a given procedure video sampled at a fixed rate. Each frame's weight is then set to account for duration variability. Specifically, the total weight of samples for a specified video is fixed such that longer videos do not influence the training more than shorter videos. At inference time, the probability is generated for every frame or, more generally, at least every sampled frame.

Block 219 illustrates loop in which if there is another image (i.e., a temporally subsequent image) included in the video of the endoscopy procedure to be analyzed then block 219 proceeds to block 205 where another image frame may be received or otherwise extracted from the video (block 205), features extracted (block 207), features filtered (block 215), and probability estimate for the temporally subsequent image generated. However, if there is not another image to be analyzed (or it is desired to see whether a transition between phases of the endoscopy procedure has occurred), then block 219 proceeds to block 221.

Block 221 shows identifying a transition in the video when the endoscopy procedure transitions from the first phase to the second phase based, at least in part, on the probability estimate for the one or more image frames. For example, the video may be segmented into phases based on the probability estimate generated for the one or more image frames. In one embodiment, image frames with the highest probability for a given phase included in the probability estimate relative to other phases are assumed to be associated with the given phase. In other embodiments the transition may be determined using a predetermined function having a maximum value indicating the time with the highest likelihood for the transition (see, e.g., FIG. 5B).

Block 223 illustrates calculating colonoscopic withdrawal time (CWT) when the endoscopy procedure is a colonoscopy. Specifically, the CWT can be estimated based, at least in part, on the transition identified when the endoscopy procedure corresponds to a colonoscopy. For example, if it is known or estimated when the video transitions from the first phase (e.g., the forward phase) to the second phase (e.g., the stagnant and/or backward phases) then the CWT may be calculated as corresponding to the elapsed time from the transition to the end of the video. However, it is appreciated that in some scenarios the withdrawal phase (i.e., the stagnant and backward phases) may be intermittently interrupted for resection of polyps. Thus, in some embodiments the CWT is further estimated by excluding the resection time of one or more polyps.

Block 225 shows calculating a performance metric based on the CWT when the endoscopy procedure is a colonoscopy. The performance metric may be generated by determining whether the CWT is sufficient or insufficient (e.g., if the CWT is at least 6 minutes in duration or a different threshold duration then the colonoscopy performance may be considered sufficient). The performance metric, along with the method 200, may allow for bulk characterization of endoscopy videos. This may enable, for example, determining whether a given physician, endoscopist, medical practitioner, medical practice, hospital, other individual, and/or other medical institution, is on average meeting the recommended guidelines for the endoscopy procedure being performed. In the case of colonoscopies, the CWT is expected to be at least 6 minutes. Accordingly, videos of all colonoscopies performed by an individual physician or for an individual medical practice could be characterized to determine an overall or average performance metric for colonoscopies. The average performance metric could then be used for training purposes, improving the quality of colonoscopies being performed, or the like. For example, if the average performance metric is insufficient due to a CWT being lower than a pre-determined threshold, the individual physician or medical practice could be notified to ensure the recommended guidelines are followed.

As illustrated in FIG. 2B, method 250 is a subset of method 200 illustrated in FIG. 2A. Specifically, for each given image included in the one or more image frames of the video being analyzed, the process block 217 proceeds to method 250 with operations being performed dependent on the expected phase of the endoscopy procedure when the given image was captured.

Block 255 illustrates identifying one or more polyps from the image frame when the first phase of the endoscopy procedure corresponds to a forward phase of a colonoscopy. As noted previously, the forward phase of the colonoscopy is characterized predominantly by forward motion of a colonoscope from the rectum toward the cecum. The one or more polyps may be detected by any commercially available polyp detection systems or otherwise identified using a classifier or other machine learning model that can identify whether the image includes a view of a polyp included in the one or more polyps. In some embodiments, the phase of the colonoscopy associated with the image may be determined based on the probability estimate generated in block 217 of method 200 illustrated in FIG. 2A.

Referring back to FIG. 2B, block 260 shows annotating a location of the one or more polyps relative to a traversal of the colonoscope during the plurality of phases of the colonoscopy. More specifically, the egomotion data 209 associated with the image frame may be used to determine a z-position of the image sensor of the colonoscopy, which can then be attributed to, or otherwise associated with, the image frame as metadata. Accordingly, the location may correspond to a frame number associated with the image frame included in the video, a temporal location such a time (e.g., the time of the video associated with the image frame), or other indicator of the relative location (i.e., in space and/or time) of the one or more polyps with respect to the video of the colonoscopy. In such a manner, the one or more polyps may be tracked both in terms of location and quantity during the forward phase of the colonoscopy.

Block 265 illustrates estimating a resection time for removal of the one or more polyps during withdrawal of a colonoscope from a cecum towards the rectum. In some embodiments, the resection time will be estimated based on the number of polyps identified during the forward phase of the colonoscopy by block 255 (e.g., based on an average time for individual polyp resection). In the same or other embodiments, the probability estimate may include a fourth probability indicative of whether a polyp resection is occurring. In other words, a fourth phase of the plurality of phases of the colonoscopy may correspond to polyp resection, which may be utilized to estimate a total time for resecting the one or more polyps.

In some embodiments, the resection time may be passed through block B to block 223 illustrated in FIG. 2A such that estimating the CWT is based, at least in part, on the transition identified and the resection time for removal of the one or more polyps. Consequently, at block 225, illustrated in FIG. 2A, the CWT is further estimated by excluding the resection time of the one or more polyps (e.g., subtracting the total time for removal of the one or more polyps from the originally determined CWT time).

Referring back to FIG. 2B, it is noted that additionally, or alternatively, method 250 will proceed to block 270 when the image frame is temporally subsequent to the first phase (e.g., the forward phase or insertion phase of the colonoscopy). In other words, when the image frame is captured when the colonoscopy is at the withdrawal phase (e.g., the second phase corresponding to the stagnant phase or the third phase corresponding to the backward phase), then the egomotion data and/or annotated location of the one or more polyps will be utilized to determine whether any of the one or more polyps are expected to be in a field of view of the colonoscope. For example, if the z-position of the colonoscope indicates a polyp was previously seen (e.g., during the forward phase), then when the colonoscope returns to the same or a similar z-position during the withdrawal phase the method 250 may output an indication that a polyp is expected to be in a field of view of the colonoscope. The indication may correspond to a visual indication (e.g., a notification displayed on display 110 illustrated in FIG. 1A or FIG. 1B), an audible notification, a haptic notification, or any other notification to alert the endoscopist.

As illustrated, the method 200 shown in FIG. 2A and the method 250 shown in FIG. 2B may generate data (e.g., egomotion data 209, landmark presence data 211, depth information 213, the probability estimate, the transition, the CWT, the performance metric, and so on). It is appreciated that the data may be output to a display, rendered for output, or otherwise provided to the endoscopist performing the endoscopy procedure or other individual reviewing endoscopy videos at any point in time or step of the methods 200 and 250. In other words, even if the methods 200 and 250 do not show an explicit step showing the output of data to be shown, rendered, or otherwise displayed, it is understood that the data may be generated and displayed in real time as the methods 200 and 250 are executed or otherwise performed.

Figure 3:
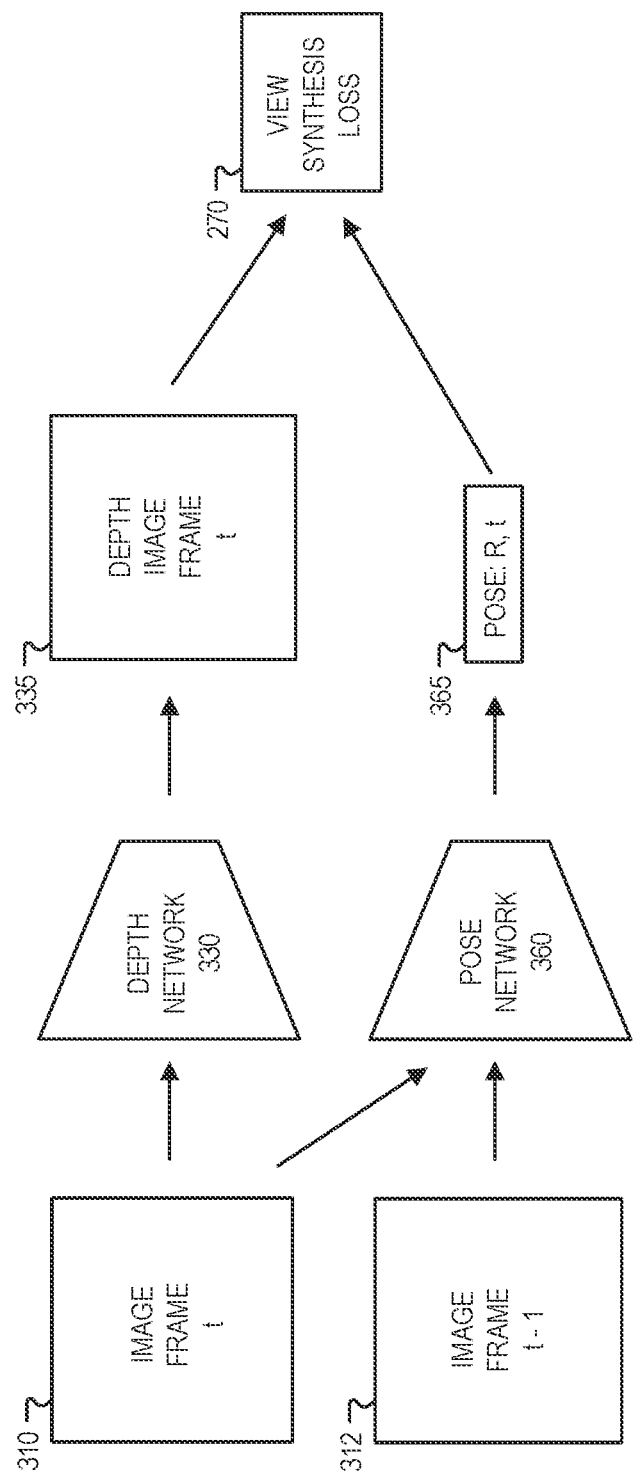
FIG. 3 illustrates an example architecture of a machine learning model including a plurality of deep neural networks, in accordance with an embodiment of the disclosure.

FIG. 3 illustrates an example architecture 300 of a machine learning model including a plurality of deep neural networks, in accordance with an embodiment of the disclosure. The architecture 300 is one possible way egomotion data and depth information may be obtained for the method 200 illustrated in FIG. 2A and FIG. 2B. The architecture 300 is a machine learning architecture utilized to concurrently determine both depth information and egomotion data via unsupervised learning since ground truth depth and egomotion data is generally unavailable in endoscopy videos. Since relative motion and depth images are closely related deep learning methods which recover them together have been utilized. The possibility of learning in an unsupervised manner is useful in the case for colonoscopy videos or other endoscopy videos since ground truth depth and motion are generally not available.

As illustrated, the network includes several sub-networks (e.g., depth network 330 and pose network 360). The depth network 330 is given an input It (e.g., the image frame 310 associated with time t of the video) and produces a depth image 335 (e.g., Dt), which corresponds to a depth map of the image frame 310. The pose network 360, given an input of the image frame 310 paired with a previously captured image frame 312 (e.g., $I_{t-1}$) produces egomotion data 365 (e.g., relative position of the camera, orientation of the camera, change in position of the camera, change in orientation of the camera, or the like). In some embodiments, the egomotion data 365 is defined as the rigid transformation (e.g., rotation matrix R and translation vector t) from the image frame 310 to the previously captured image frame 312. In some embodiments, an additional intrinsics network may be used to produce an estimate of the internal calibration K; or alternatively, a pre-learned K can be given as an input.

In some embodiments, the relationship between the geometric location of corresponding pixels in two image frames (consecutive or otherwise) may be expressed by combining the depth, pose, and intrinsics information as:

$$z'p'=KRK^{-1}zp+Kt$$

where p and p' are the corresponding pixels in homogeneous coordinates and z and z' are their corresponding depth values. The view synthesis loss 270 then compares the RGB values of the pixels at p in the previously captured image frame 312 ($I_{t-1}$) and p' in the image frame 310 ($I_t$). In some embodiments, the loss function is the Li loss of the RGB difference combined with an analogous loss based on structural similarity (SSIM).

Figure 4A:
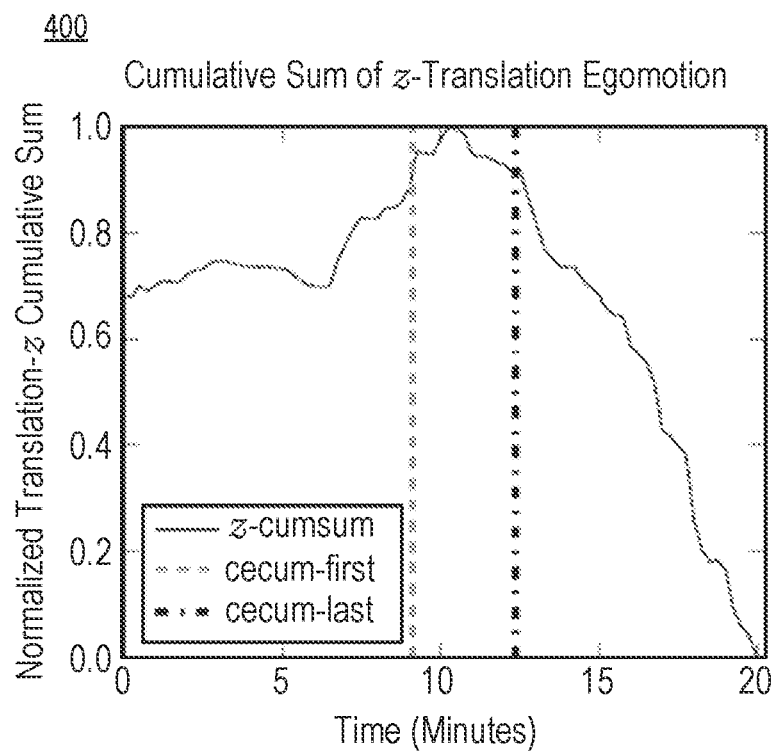
FIGS. 4A and 4B illustrate example charts illustrating features extracted with respect to elapsed time of an endoscopy procedure, in accordance with an embodiment of the disclosure.
Figure 4B:
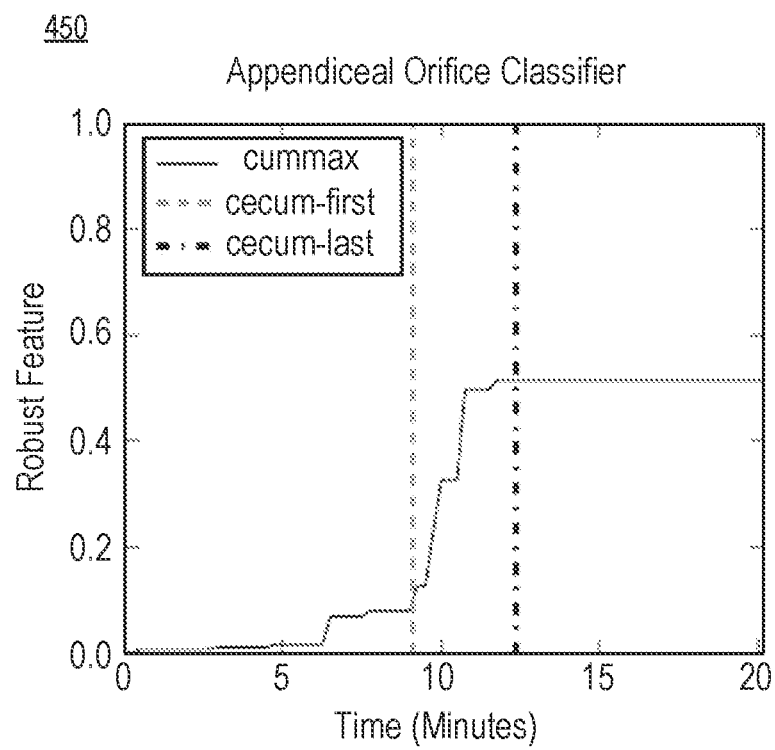

FIGS. 4A and 4B illustrate example charts 400 and 450 illustrating features extracted with respect to elapsed time of an endoscopy procedure, in accordance with an embodiment of the disclosure. For each of the charts 400 and 450, the time at which the cecum was first and last observed are annotated to provide a general idea as to where the withdrawal phase (e.g., combination of the stagnant and backward phases) is expected to start. In other words, the transition from the insertion phase to the withdrawal phase may occur at some point near where the cecum was first observed.

As illustrated in FIG. 4A, chart 400 shows the cumulative sum of the z-translation egomotion data that has been normalized with respect to time (e.g., elapsed time of the colonoscopy or the video). As discussed previously, the cumulative sum of the z-translation may correspond to normalized exponentially weighted moving average determined based on features extracted from image frames analyzed by the method 200 and 250 illustrated in FIG. 2A and FIG. 2B.

In the illustrated embodiment shown by FIG. 4B, chart 450 show the filtered output of the appendiceal orifice classifier, which may be included in one of a plurality of deep neural networks for classifying whether image frames include the appendiceal orifice. It is appreciated that the robust feature may correspond to the exponentially weighted moving average that the appendiceal orifice has been observed.

Thus, as shown in the chart 450, the robust feature increases with time until the appendiceal orifice is expected to have been observed, but does not decrease since the filtered feature from the landmark presence data is based on the cumulative maximum of the filtered feature. In other words, the robust feature primarily considers whether the anatomical landmark has been observed over time rather than if a singular image frame includes a view of the anatomical landmark.

Figure 5A:
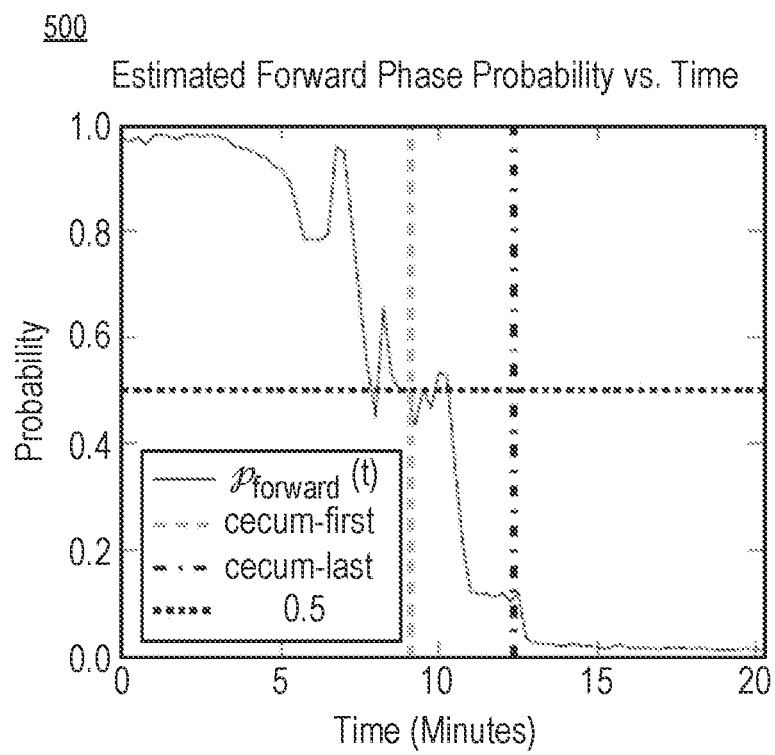
FIG. 5A illustrates an example chart showing estimated forward phase probability with respect to elapsed time of an endoscopy procedure, in accordance with an embodiment of the disclosure.

FIG. 5A illustrates an example chart 500 showing estimated forward phase probability (e.g., from the probability estimate generated in block 217 of FIG. 2A) with respect to elapsed time of an endoscopy procedure, in accordance with an embodiment of the disclosure. Each value of the probability at each point is time is associated with a respective image frame included in the video of the colonoscopy and indicates a likelihood that the image frame associated with the corresponding time was captured when the colonoscopy was at the forward phase (e.g., the first phase and/or colonoscopic insertion phase). As expected during the forward phase, the colonoscope may have both forward and backwards motion as the colonoscope is pushed through flexures of the colon, which is indicated by the intermittent increasing and decreasing values of the probability over time. However, as the forward motion is predominantly characterized by forward z-motion, the probability gradually decreases towards zero over time due to the colonoscopy transitioning from the forward phase to the stagnant and backward phases.

Figure 5B:
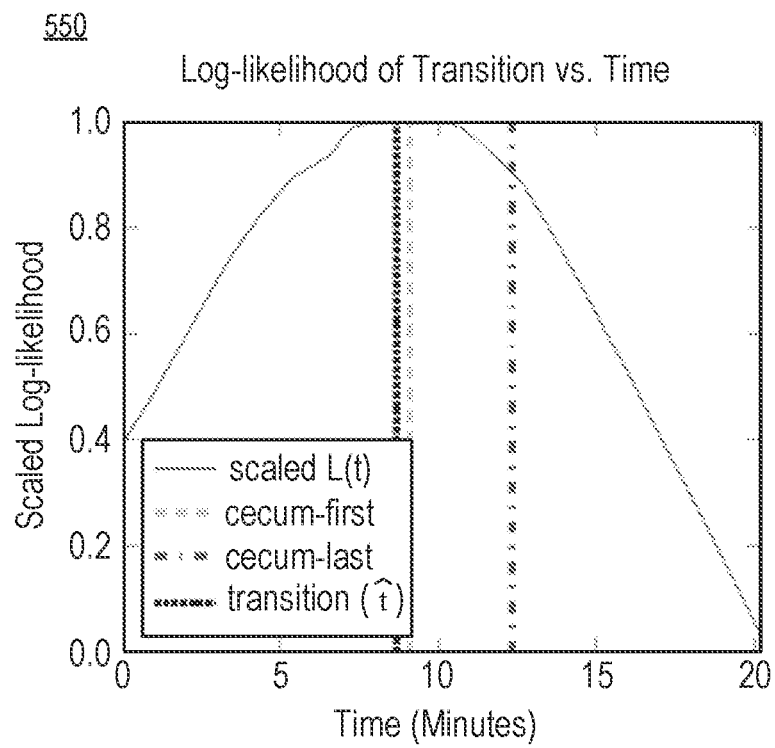
FIG. 5B illustrates a log-likelihood of transition from a first phase to a second phase of the endoscopy procedure with respect to elapsed time of the endoscopy procedure, in accordance with an embodiment of the disclosure.

FIG. 5B illustrates an example chart 550 showing a log-likelihood of transition from a first phase to a second phase of the endoscopy procedure with respect to elapsed time of the endoscopy procedure, in accordance with an embodiment of the disclosure. Specifically, the transition may be calculated using the probability estimate generated collectively for the video of the endoscopy procedure (e.g., each image frame or some subsampled set of image frames from the video is characterized and a corresponding probability estimate is generated as shown in FIG. 2A). The probability estimate may then be represented with respect to time and phase as $\hat{p}_{c,\,t}$, where c indicates the phase and t indicates the relative time the image frame was captured. For two phases, the log-likelihood of the transition occurring at time t can be denoted by L(t), which can be written as:

$$L(t) = \Sigma_{t' \leq t} \log \hat{p}_{1,t'} + \Sigma_{t' > t} \log \hat{p}_{2,t'}.$$

The log-likelihood (and the rest of the analysis) can be similarly extended into two split phases.

In some embodiments, the transition, $\hat{t}$, is chosen such that $\hat{t} = \mathrm{argmax}_t L(t)$. It is appreciated that if there are multiple points that satisfy argmax, then the temporally earlier one may be selected. An online computational method may then be utilized to determine $\hat{t}$. To this end, V[c,t] is defined as the value of the optimal log-likelihood for the 1, 2, . . . , t frames, which end with the phase c. Then the condition of V[1,0]=V[2,0] is set and $$V[1,t] = V[1, t-1] + \log(\hat{p}_{1,t})$$

$$V[2,t] = \max(V[1, t-1], V[2,t-1]) + \log(\hat{p}_{2,t}).$$

Finally, L($\hat{t}$) can be set to equal V[2,T], where T is the index of the last frame. The value can then be retrieved by setting $\hat{t}=t$, where t is the last index for which V[1, t−1]>V[2, t−1].

It is appreciated that the above equation can be extended to accommodate any number of phases (e.g., 3 or more).

As illustrated in FIG. 5B, L(t) is visualized by chart 550, which shows the transition when the colonoscopy video changes from the forward phase (e.g., first phase) to the withdrawal phase (e.g., second phase). As discussed above, the transition occurs at the maximum of L(t), which is shown by a black vertical line.

Figure 6:
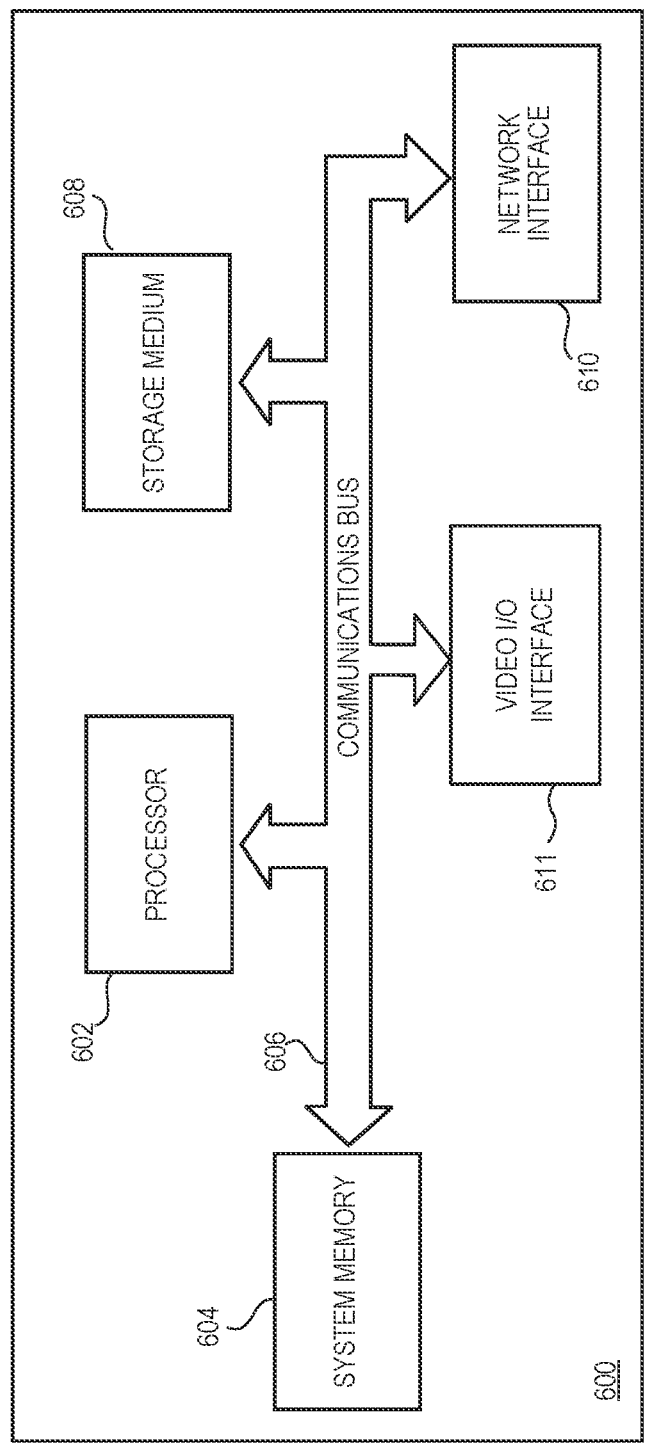
FIG. 6 is a functional block diagram illustrating a demonstrative computing device for implementing an endoscopy video assistant, in accordance with any embodiment of the disclosure.

FIG. 6 is a block diagram that illustrates aspects of a demonstrative computing device 600 appropriate for implementing EVA 115 illustrated in FIG. 1B, the method 200 illustrated in FIG. 2A, or the method 250 illustrated in FIG. 2B, in accordance with embodiments of the present disclosure. Those of ordinary skill in the art will recognize that computing device 600 may be implemented using currently available computing devices or yet to be developed devices.

In its most basic configuration, computing device 600 includes at least one processor 602 and a system memory 604 connected by a communication bus 606. Depending on the exact configuration and type of device, system memory 604 may be volatile or nonvolatile memory, such as read only memory ("ROM"), random access memory ("RAM"), EEPROM, flash memory, or similar memory technology. Those of ordinary skill in the art will recognize that system memory 604 typically stores data and/or program modules that are immediately accessible to and/or currently being operated on by the processor 602. In this regard, the processor 602 may serve as a computational center of computing device 600 by supporting the execution of instructions.

As further illustrated in FIG. 6, computing device 600 may include a network interface 610 comprising one or more components for communicating with other devices over a network. Embodiments of the present disclosure may access basic services that utilize network interface 610 to perform communications using common network protocols. Network interface 610 may also include a wireless network interface configured to communicate via one or more wireless communication protocols, such as WiFi, 2G, 3G, 4G, LTE, WiMAX, Bluetooth, and/or the like.

In the exemplary embodiment depicted in FIG. 6, computing device 600 also includes a storage medium 608. However, services may be accessed using a computing device that does not include means for persisting data to a local storage medium. Therefore, the storage medium 608 may be omitted. In any event, the storage medium 608 may be volatile or nonvolatile, removable or nonremovable, implemented using any technology capable of storing information such as, but not limited to, a hard drive, solid state drive, CD-ROM, DVD, or other disk storage, magnetic cassettes, magnetic tape, magnetic disk storage, and/or the like.

The illustrated embodiment of computing device 600 further includes a video input/out interface 611. Video I/O interface 611 may include an analog video input (e.g., composite video, component video, VGG connector, etc.) or a digital video input (e.g., HDMI, DVI, DisplayPort, USB-A, USB-C, etc.) to receive the live video feed from colonoscope 105 and a similar type of video output port to output the live video feed within colonoscopy UI 150 to display 110. In one embodiment, video I/O interface 611 may also represent a graphics processing unit capable of performing the necessary computational video processing to generate and render colonoscopy UI 150.

As used herein, the term "computer-readable medium" includes volatile and non-volatile and removable and non-removable media implemented in any method or technology capable of storing information, such as computer-readable instructions, data structures, program modules, or other data. In this regard, the system memory 904 and storage medium 908 depicted in FIG. 9 are merely examples of computer-readable media.

Suitable implementations of computing devices that include a processor 602, system memory 604, communication bus 606, storage medium 608, and network interface 610 are known and commercially available. For ease of illustration and because it is not important for an understanding of the claimed subject matter, FIG. 6 does not show some of the typical components of many computing devices. In this regard, the computing device 600 may include input devices, such as a keyboard, keypad, mouse, microphone, touch input device, touch screen, tablet, and/or the like. Such input devices may be coupled to computing device 600 by wired or wireless connections including RF, infrared, serial, parallel, Bluetooth, USB, or other suitable connection protocols using wireless or physical connections. Since these devices are well known in the art, they are not illustrated or described further herein.

The above user-interface has been described in terms of a colonoscopy and is particularly well-suited as a colonoscopy user-interface to aid visualization of colonoscopy procedures and/or analysis of colonoscopy videos. However, it should be appreciated that user-interface 150 may be more broadly/generically described as an endoscopy user-interface that may be used to visualize endoscopy procedures, in general, related to other anatomical structures and/or analyze endoscopy videos. For example, the methods 200 and 250 are applicable for analyzing other gastroenterological procedures including endoscopy procedures within the upper and lower gastrointestinal tracts. In yet other examples, the methods 200 and 250 may be used to analyze videos of non-gastroenterological procedures that may occur in the esophagus, bronchial tubes, other tube-like anatomical structures, etc.

The processes and user-interface described above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, some of the processes or logic for implementing the user-interface may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory machine-accessible storage medium that provides instructions that, when executed by a machine, will cause the machine to perform operations comprising:
   receiving a plurality of image frames associated with a video of an endoscopy procedure, wherein the endoscopy procedure includes a plurality of phases including a first phase and a second phase;
   generating a probability estimate for one or more image frames included in the plurality of image frames, wherein the probability estimate includes a first probability the one or more image frames are associated with the first phase of the endoscopy procedure; and
   identifying a transition in the video when the endoscopy procedure transitions from the first phase to the second phase based, at least in part, on the probability estimate for the one or more image frames.

2. The at least one non-transitory machine-accessible storage medium of claim 1, wherein the plurality of phases further includes a third phase, wherein the probability estimate further includes a second probability the one or more image frames are associated with the second phase, and wherein the probability estimate further includes a third probability the one or more image frames are associated with the third phase.

3. The at least one non-transitory machine-accessible storage medium of claim 2, wherein the endoscopy procedure is a colonoscopy, wherein the first phase corresponds to a forward phase characterized predominantly by forward motion of a colonoscope from a rectum toward a cecum, wherein the second phase corresponds to a stagnant phase when the colonoscope reaches the cecum, and wherein the third phase corresponds to a backward phase characterized predominantly by backward motion of the colonoscope when the colonoscope is withdrawn from the cecum towards the rectum.

4. The at least one non-transitory machine-accessible storage medium of claim 1, providing additional instructions that, when executed by the machine, will cause the machine to perform further operations, comprising:
   estimating a colonoscopic withdrawal time (CWT) based, at least in part, on the transition identified when the endoscopy procedure corresponds to a colonoscopy.

5. The at least one non-transitory machine-accessible storage medium of claim 4, providing additional instructions that, when executed by the machine, will cause the machine to perform further operations, comprising:
   generating a performance metric associated with the colonoscopy based on the CWT.

6. The at least one non-transitory machine-accessible storage medium of claim 4, providing additional instructions that, when executed by the machine, will cause the machine to perform further operations, comprising:
   identifying one or more polyps during the first phase when the first phase corresponds to a forward phase of a colonoscopy characterized predominantly by forward motion of a colonoscope from a rectum toward a cecum;
   estimating a resection time for removal of the one or more polyps during withdrawal of a colonoscope from a cecum towards the rectum, and wherein the CWT is further estimated by excluding the resection time of the one or more polyps.

7. The at least one non-transitory machine-accessible storage medium of claim 1, providing additional instructions that, when executed by the machine, will cause the machine to perform further operations, comprising:
identifying one or more polyps during the first phase when the first phase corresponds to a forward phase of a colonoscopy characterized predominantly by forward motion of a colonoscope from a rectum toward a cecum;
annotating a location of the one or more polyps relative to a traversal of the colonoscope during the plurality of phases of the colonoscopy; and
outputting an indication when the one or more polyps are expected to be in a field of view of the colonoscope based on the traversal of the colonoscope for one or more phases included in the plurality of phases that are subsequent to the first phase.

8. The at least one non-transitory machine-accessible storage medium of claim 1, wherein the probability estimate is generated with a machine learning model including a plurality of deep neural networks to receive the one or more image frames.

9. The at least one non-transitory machine-accessible storage medium of claim 8, providing additional instructions that, when executed by the machine, will cause the machine to perform further operations, comprising:
extracting different features with the plurality of deep neural networks in response to the machine learning model receiving the one or more image frames, wherein the different features are determined on a per-frame basis with each feature included in the different features associated with a corresponding neural network included in the plurality of deep neural networks.

10. The at least one non-transitory machine-accessible storage medium of claim 9, wherein the different features characterize the one or more image frames with a reduced representation relative to a pixel value quantity of the one or more image frames.

11. The at least one non-transitory machine-accessible storage medium of claim 9, providing additional instructions that, when executed by the machine, will cause the machine to perform further operations, comprising:
applying one or more smoothing filters to the different features to generate smoothed features that aggregate the different features over multiple frames included in the one or more image frames, and wherein the probability estimate is based on the smoothed features.

12. The at least one non-transitory machine-accessible storage medium of claim 11, wherein the one or more smoothing filters includes an exponentially weighted moving average of one or more of the different features.

13. The at least one non-transitory machine-accessible storage medium of claim 11, wherein the machine learning model further includes:
a third deep neural network included in the plurality of deep neural networks to extract depth information associated with the one or more image frames, wherein the one or more image frames are provided in parallel to the first deep neural network, the second deep neural network, and the third deep neural network to concurrently determine each of the different features for the one or more image frames.

14. The at least one non-transitory machine-accessible storage medium of claim 9, wherein the machine learning model includes:
a first deep neural network included in the plurality of deep neural networks to extract egomotion data included in the different features, wherein the egomotion data corresponds to an estimated motion of an endoscope camera associated with capture of the one or more image frames; and
a second deep neural network included in the plurality of deep neural networks to extract landmark presence data included in the different features, wherein the landmark presence data corresponds to an indication of whether the one or more image frames include a view of one or more anatomical landmarks associated with the endoscopy procedure.

15. The at least one non-transitory machine-accessible storage medium of claim 14, wherein the one or more anatomical landmarks associated with the endoscopy procedure include at least one of an appendiceal orifice, a triradiate fold, or an ileocecal valve when the endoscopy procedure corresponds to a colonoscopy.

16. The at least one non-transitory machine-accessible storage medium of claim 9, wherein the machine learning model further includes a phase classifier to receive the different features and in response output the probability estimate for the one or more image frames on a per-frame basis.

17. The at least one non-transitory machine-accessible storage medium of claim 1, providing additional instructions that, when executed by the machine, will cause the machine to perform further operations, comprising:
extracting features representative of the plurality of the image frames using a plurality of neural networks, wherein the features includes egomotion data, landmark presence data, and depth information, and wherein the probability estimate for the one or more image frames is based on the features.

18. A system, comprising:
an endoscope including an image sensor to capture a plurality of image frames associated with a video of an endoscopy procedure, wherein the endoscopy procedure includes a plurality of phases including a first phase and a second phase;
a controller coupled to the endoscope to receive the plurality of image frames from the image sensor, wherein the controller includes logic that when executed by the controller causes the system to perform operations including:
generating a probability estimate for one or more image frames included in the plurality of image frames, wherein the probability estimate includes a first probability the one or more image frames are associated with the first phase; and
identifying a transition in the video when the endoscopy procedure transitions from the first phase to the second phase based, at least in part, on the probability estimate for the one or more image frames.

19. The system of claim 18, wherein the controller includes additional logic that when executed by the controller causes the system to perform further operations including:
identifying one or more polyps during the first phase when the first phase corresponds to a forward phase of a colonoscopy characterized predominantly by forward motion of the endoscope from a rectum toward a cecum;

annotating a location of the one or more polyps relative to a traversal of the endoscope during the plurality of phases of the colonoscopy; and outputting an indication when the one or more polyps are expected to be in a field of view of the endoscope based on the traversal of the endoscope for one or more phases included in the plurality of phases that are subsequent to the first phase.

20. A computer-implemented method, comprising:

receiving a plurality of image frames associated with a video of an endoscopy procedure, wherein the endoscopy procedure includes a plurality of phases including a first phase and a second phase;

generating a probability estimate for one or more image frames included in the plurality of image frames, wherein the probability estimate includes a first probability one or more image frames are associated with the first phase; and identifying a transition in the video when the endoscopy procedure transitions from the first phase to the second phase based, at least in part, on the probability estimate for the one or more image frames.

21. The computer-implemented method of claim 20, wherein the plurality of phases further includes a third phase, wherein the probability estimate further includes a second probability the one or more image frames are associated with the second phase, wherein the probability estimate further includes a third probability the one or more image frames are associated with the third phase, wherein the endoscopy procedure is a colonoscopy, wherein the first phase corresponds to a forward phase characterized predominantly by forward motion of a colonoscope from a rectum toward a cecum, wherein the second phase corresponds to a stagnant phase when the colonoscope reaches the cecum, and wherein the third phase corresponds to a backward phase characterized predominantly by backward motion of the colonoscope when the colonoscope is withdrawn from the cecum towards the rectum.

* * * * *